United States Patent
Lin et al.

(10) Patent No.: US 9,441,191 B2
(45) Date of Patent: Sep. 13, 2016

(54) OMNI-FUNCTIONAL HIGH-EFFICIENT SOLID-STATE FERMENTATION METHOD FOR EDIBLE AND MEDICINAL MICROORGANISMS

(71) Applicant: TAIWAN LEADER BIOTECH CORP., Taipei (TW)

(72) Inventors: Chin-Chung Lin, Taipei (TW); Yu-Yen Lin, Taipei (TW); Jong-Tar Kuo, Taipei (TW); Chien-Chang Liao, Taipei (TW); Jent-turn Lee, Taipei (TW); Yu-Chieh Chu, Taipei (TW)

(73) Assignee: TAIWAN LEADER BIOTECH CORP., Taipei (TW)

( * ) Notice: Subject to any disclaimer, the term of this patent is extended or adjusted under 35 U.S.C. 154(b) by 219 days.

(21) Appl. No.: 14/296,637

(22) Filed: Jun. 5, 2014

(65) Prior Publication Data

US 2015/0353879 A1    Dec. 10, 2015

(51) Int. Cl.
  *C12M 1/16*    (2006.01)
  *C12M 3/00*    (2006.01)
  *C12M 1/00*    (2006.01)
  *C12M 1/12*    (2006.01)

(52) U.S. Cl.
  CPC .............. *C12M 21/16* (2013.01); *C12M 23/04* (2013.01); *C12M 23/22* (2013.01); *C12M 23/34* (2013.01); *C12M 23/48* (2013.01); *C12M 29/06* (2013.01); *C12M 47/14* (2013.01)

(58) Field of Classification Search
  CPC .... C12M 21/16; C12M 23/04; C12M 23/48; C12M 23/52; C12M 25/06; C12M 33/00; A01G 1/04; A01G 1/042
  See application file for complete search history.

(56) References Cited

U.S. PATENT DOCUMENTS

| | | | | |
|---|---|---|---|---|
| 3,756,784 A | * | 9/1973 | Pittwood | C05F 17/0252 34/173 |
| 4,273,495 A | * | 6/1981 | Pannell | A01G 1/044 141/125 |
| 4,674,228 A | * | 6/1987 | Murata | A01G 1/042 47/1.1 |
| 4,857,464 A | * | 8/1989 | Weathers | C12M 21/08 435/289.1 |
| 4,901,471 A | * | 2/1990 | van den Top | A01G 1/042 414/268 |

(Continued)

FOREIGN PATENT DOCUMENTS

| | | | |
|---|---|---|---|
| JP | 04079813 A | * | 3/1992 |
| JP | 06007032 A | * | 1/1994 |

*Primary Examiner* — William H Beisner
(74) *Attorney, Agent, or Firm* — Jackson IPG PLLC; Demian K. Jackson

(57) ABSTRACT

A solid-state fermentation method is provided. The method is provided for edible and medicinal microorganisms. A commensurate device is used for processing sterilization, inoculation, cultivation, drying, and collection. Cultivation substrates are filled in cultivation plates and placed on trays of a movable layer rack in a reaction fermenter for fermentation. Inner pipes provide inoculation, fluid nutrient, and air for fermentation of microorganisms. The reaction fermenter is accompanied with a dry circulation unit and a production collection unit for drying and collection. The solid-state fermentation processes are thus effectively integrated without the need of transferring fermented products between stations, which largely reduces contamination rate. Even more, there is no need to purchase automatic production equipments of high mechanical technologies. Thus, the present invention reduces labor requirement, saves time and energy, deducts cost of automatic equipments, achieves low contamination rate, and processes automatic mass production even without automatic production equipments.

7 Claims, 3 Drawing Sheets

(56) References Cited

U.S. PATENT DOCUMENTS

| | | | | |
|---|---|---|---|---|
| 4,963,353 A | * | 10/1990 | Sidhu | A61K 8/975 424/195.15 |
| 6,018,906 A | * | 2/2000 | Pia | A01G 1/042 47/1.1 |
| 6,620,614 B1 | * | 9/2003 | Luth | C12M 21/16 435/291.3 |
| 7,531,350 B2 | * | 5/2009 | Shiau | C12M 21/16 435/292.1 |
| 2007/0144064 A1 | * | 6/2007 | Toto | A01G 1/042 47/17 |
| 2011/0258915 A1 | * | 10/2011 | Subhadra | C12M 21/02 44/385 |

\* cited by examiner

OMNI-FUNCTIONAL HIGH-EFFICIENT SOLID-STATE FERMENTATION METHOD FOR EDIBLE AND MEDICINAL MICROORGANISMS

FIELD OF THE INVENTION

The present invention relates to solid-state fermentation; more particularly, relates to integrally conducting production processes of solid-state fermentation, including sterilization, inoculation, cultivation, drying, and collection, where time and energy are saved; cost is low; operation is simple; labor force demand is less; contamination rate is reduced; and automatic mass production is processed even without automatic production equipments.

DESCRIPTION OF THE RELATED ART

Presently, the solid-state fermentation devices are categorized into the following types. The first type is a gas-solid fluidized bed fermenter. This type of fermenter is typically a stand-alone tank. Inside the tank, solid cultivation substrates are filled and are agitated and overturned by an agitator. A ventilation pipe is externally connected to the tank for air circulation and temperature reduction. A spraying mechanism is provided for moisturizing from top of the tank. However, this type of devices are considerably energy consuming, the cultivation substrate is susceptible to be squeezes and broken, and the container volume of the tank is limited to a height stackable for the cultivation substrate. The second type is a rotary drum fermenter. This type of fermenter usually has cylindrical structures, in which the cultivation substrate is overturned by 360 degrees of rotation with air and liquid nutrient supplied. However, such a fermenter may not process fermentation in more than ⅓ volume of its container. Hence, this type of fermenter has limited use and is expensive and energy consuming. Furthermore, disturbance resulted from the rotation process of the fermenter might adversely affect growth of the microorganisms which are required to be placed and maintained still; and, not to mention, the cultivation substrate might form bumps. The third type is a tray fermenter. In this type of fermenter, a cultivation substrate is filled in each fermenter plate and the fermenter plates are placed on trays of a corresponding layer rack in the fermenter tank one by one. In U.S. Pat. No. 6,620,614 B1, the fermenter provides an efficient heat evacuation ability, and supplies air and liquid nutrient by using a pipe. It also provides a proper growth environment to microorganisms which are required to be placed and maintained still. However, the prior art is considerably labor consuming in installation and product collection. The integration on production processes is not good. Although there is another prior art which tries to integrate the production processes, the fermenter used is too complex in design and is costly. Consequently, there is no solid-state tray fermenter with production processes, from sterilization to collection, excellently integrated in a simple design.

Hence, the prior arts do not fulfill all users' requests on actual use.

SUMMARY OF THE INVENTION

The main purpose of the present invention is to integrally conduct production processes of solid-state fermentation, including sterilization, inoculation, cultivation, drying, and collection, where time and energy are saved; cost is low; operation is simple; labor force demand is less; contamination rate is reduced; and automatic mass production may be processed even without automatic production equipments.

To achieve the above purpose, the present invention is an omni-functional high-efficient solid-state fermentation method for edible and medicinal microorganisms, comprising steps of: (a) providing a solid-state fermentation device, where the device has an integrated production procedure of solid-state fermentation and comprises a reaction fermenter, a layer rack, at least one cultivation plate, a fluid pipeline, a gas pipeline, and a product collection unit, where the reaction fermenter has an observation window at a lateral side and an opening lid at a front side; where the layer rack is movable, located in the reaction fermenter, hollowed out at bottom and has at least one supporting layer; where the cultivation plate is located in the layer rack and each of the cultivation plate is located on the supporting layer and has a bottom tray; where the fluid pipeline is located in the reaction fermenter and comprises a fluid pipe and a fluid outlet; where the fluid pipe has a fluid inlet and is connected with a plurality of spraying ducts; where every one of the spraying ducts is located above one of the supporting layer, separately; where the gas pipeline is located in the reaction fermenter and comprises a gas pipe and a gas outlet; where the gas pipe has a gas inlet and is connected with a plurality of gas ducts; where every one of the gas ducts is located between two adjacent ones of the supporting layer, separately; and where the product collection unit comprises a collection tray and the collection tray is located at bottom in the reaction fermenter and is inclined inwardly to obtain a funnel-like shape; (b) providing a plurality of cultivation substrates, where every one of the cultivation substrates is filled in one of the cultivation plate, separately; (c) directing a fluid into the fluid pipe through the fluid inlet; dividing the flow of the fluid into each of the spraying ducts; uniformly spraying the fluid on each of the cultivation plate by each of the spraying ducts to supply inoculums or provide the liquid nutrient which is required on fermenting microorganisms; and leaking out residual portion of the fluid through the fluid outlet at bottom in the reaction fermenter; (d) directing a gas into the gas pipe through the gas inlet; dividing the flow of the gas into each of the gas ducts; uniformly spreading the gas on each of the cultivation plate by each of the gas ducts to provide the gas oxygen-enriched, control temperature, and dissipate the heat which are required on fermenting the microorganisms; and leaking out residual portion of the gas through the gas outlet on top in the reaction fermenter; and (e) examining a fermenting state and a growth state of the microorganisms, processing a drying process after fermenting the microorganisms, and collecting the dried cultivation substrate by using the collection tray to obtain a fermented product. Accordingly, a novel omni-functional high-efficient solid-state fermentation method for edible and medicinal microorganisms is obtained.

BRIEF DESCRIPTIONS OF THE DRAWINGS

The present invention will be better understood from the following detailed descriptions of the preferred embodiments according to the present invention, taken in conjunction with the accompanying drawings, in which.

DESCRIPTION OF THE PREFERRED EMBODIMENTS

Figure 1:
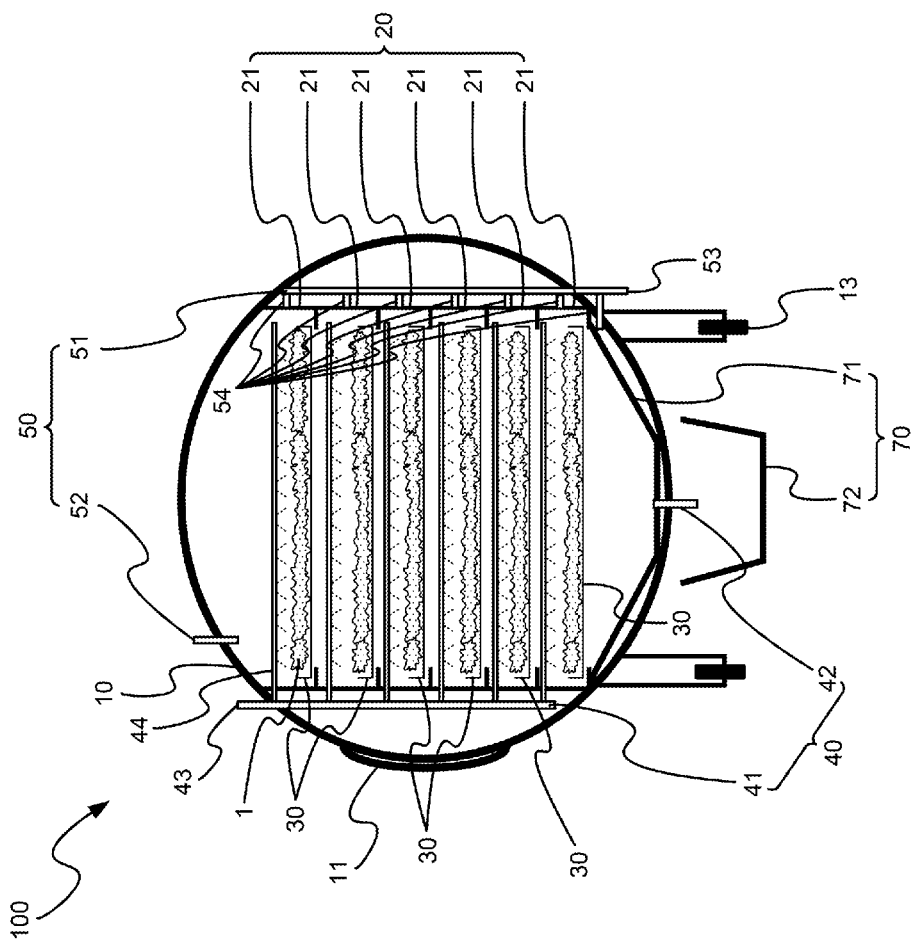
FIG. 1 is the frontward sectional view showing the device used in the preferred embodiment according to the present invention.
Figure 2:
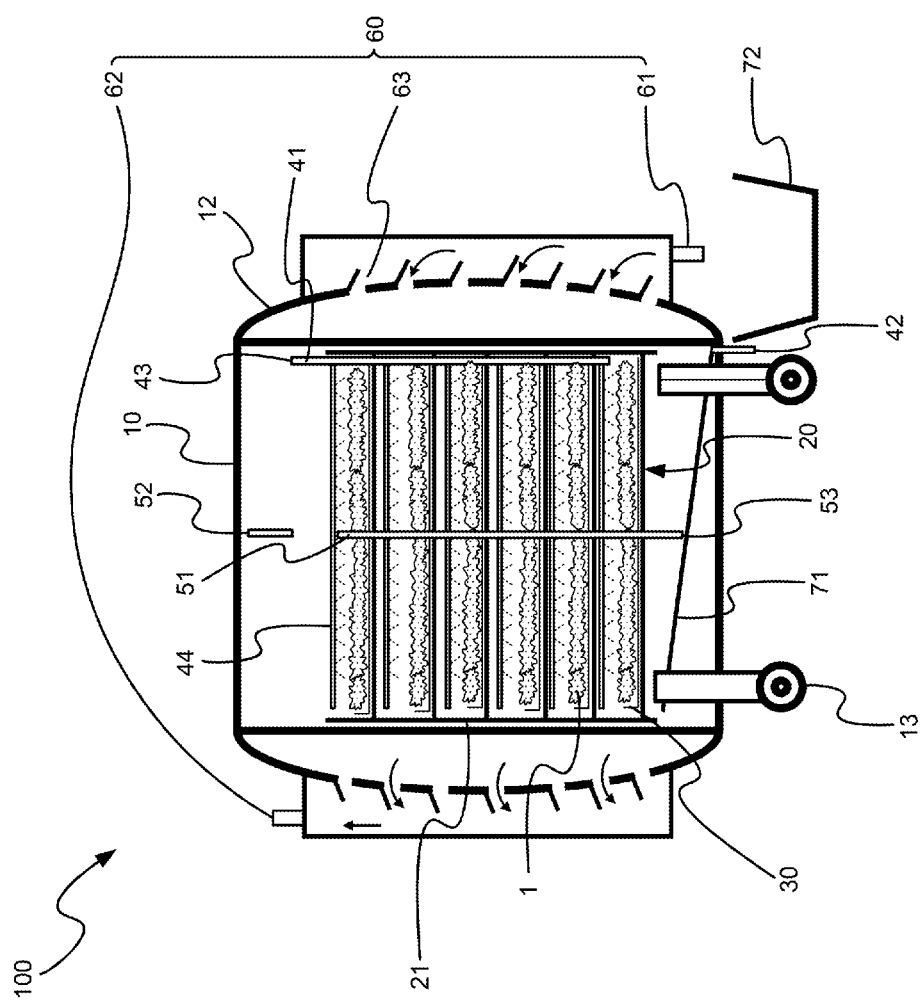
FIG. 2 is the sideward sectional view showing the device.
Figure 3:
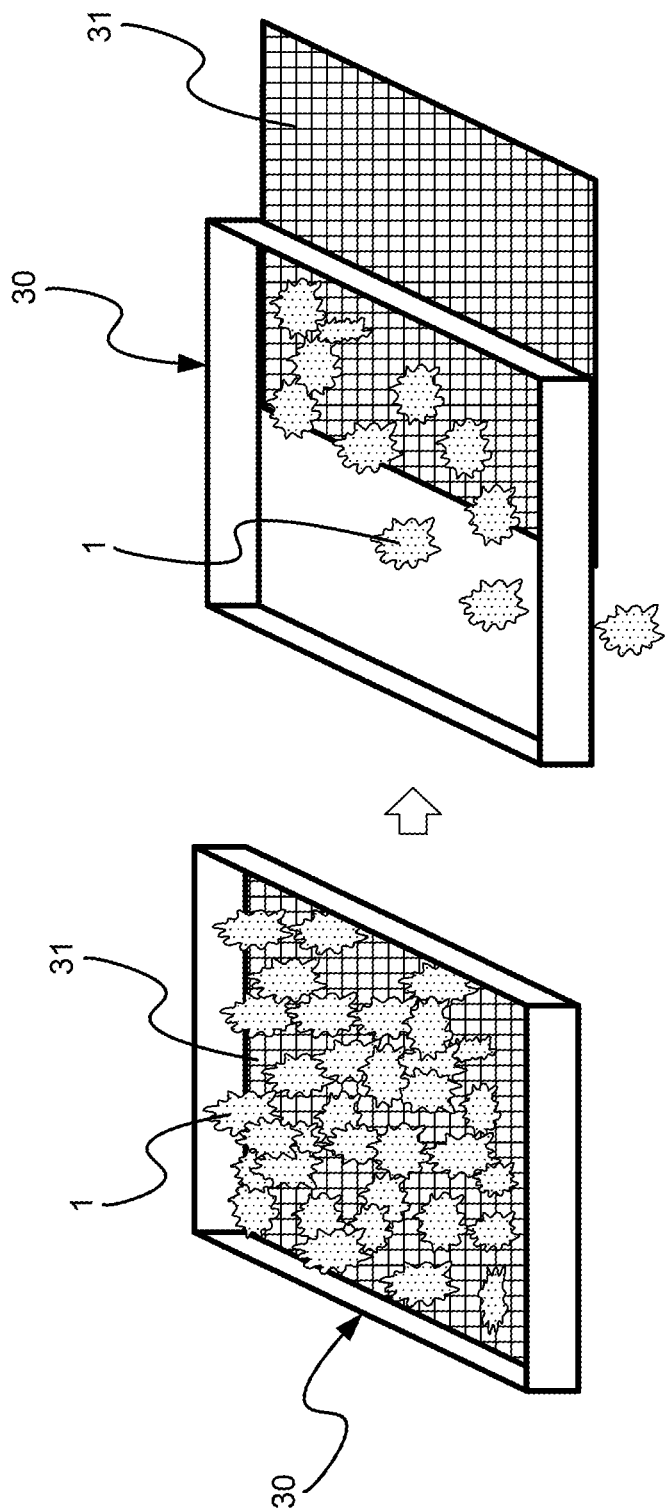
FIG. 3 is the view showing the state of use of the bottom tray.

Please refer to FIG. 1 to FIG. 3, which are a frontward sectional view showing a device used in a preferred embodiment according to the present invention; a sideward sectional view showing the device; and a view showing a state of use of a bottom tray. As shown in the figures, the present invention is an omni-functional high-efficient solid-state fermentation method for edible and medicinal microorganisms, where a device used for the present invention provides the fermentation method for edible and medicinal microorganisms and the method comprises the following steps:

(a) An omni-functional solid-state fermentation device 100 is provided, which device has an integrated production procedure, including sterilization, inoculation, cultivation, drying, and collection. The device 100 comprises a reaction fermenter 10, a layer rack 20, at least one cultivation plate 30, a fluid pipeline 40, a gas pipeline 50, a dry circulation unit 60 and a product collection unit 70. Therein, the reaction fermenter 10 has an observation window 11 at a lateral side and an opening lid 12 at a front side; the layer rack 20 is movable, set in the reaction fermenter 10, hollowed out at bottom and has at least one supporting layer 21; each of the cultivation plate 30 is put in the layer rack 20, placed on the supporting layer 21 and has a bottom tray 31; the fluid pipeline 40 is set in the reaction fermenter 10 and comprises a fluid pipe 41 and a fluid outlet 42; the fluid pipe 41 has a fluid inlet 43 and is connected with a plurality of spraying ducts 44; every one of the spraying ducts 44 is set above one of the supporting layer 21, separately; the gas pipeline 50 is set in the reaction fermenter 10 and comprises a gas pipe 51 and a gas outlet 52; the gas pipe 51 has a gas inlet 53 and is connected with a plurality of gas ducts 54; every one of the gas ducts 54 is set between two adjacent ones of the supporting layer 21, separately; the dry circulation unit 60 comprises a hot dry gas inlet 61, a hot dry gas outlet 62 and a plurality of hot gas distribution holes 63; the hot dry gas inlet 61 is set with the opening lid 12 at the front side of the reaction fermenter 10; the hot dry gas outlet 62 is set at a rear side of the reaction fermenter 10; the hot gas distribution holes 63 are set at the front side and the rear side of the reaction fermenter 10; each of the hot gas distribution holes 63 is corresponding to at least one of the supporting layer 21; the dry circulation unit 60, thus, forms an effective dry circulation for processing drying after directing hot dry air; the product collection unit 70 comprises a collection tray 71 and a collection bucket 72; the collection tray 71 is set at bottom in the reaction fermenter 10 and is inclined inwardly to obtain a funnel-like shape; and, the collection bucket 72 is set at bottom outside the reaction fermenter 10.

(b) A plurality of cultivation substrates 1 are provided with each filled in a cultivation plate 30.

(c) A fluid is directed into the fluid pipe 41 through the fluid inlet 43, where the fluid is divided into each of the spraying duct 44; and where the fluid is evenly sprayed by the spraying duct 44 on each of the cultivation plate 30 to supply inoculums or add a liquid nutrient which is required on fermenting microorganisms. Residual portion of the fluid is leaked out through the fluid outlet 42 at bottom in the reaction fermenter 10.

(d) A gas is directed into the gas pipe 51 through the gas inlet 53, where the gas is divided into each of the gas ducts 54, and the gas is spread into each of the cultivation plate 30 to supply air, control temperature and dissipate heat for supplying enough oxygen concentration required on fermenting microorganisms. Residual portion of the gas is exhausted through the gas outlet 52 on top in the reaction fermenter 10.

(e) A fermenting state and a growth state of the microorganisms are examined through the observation window 11. The cultivation substrate 1 is dried after the fermentation to be collected by using the product collection unit 70 for obtaining a fermented product.

Thus, a novel omni-functional high-efficient solid-state fermentation method for edible and medicinal microorganisms is obtained.

The reaction fermenter 10 is integrally formed and has a cylinder or rectangular shape. The reaction fermenter 10 is a movable tank with a wheel 13, by which the reaction fermenter 10 is moved to a tunnel sterilizer (not shown in the figures) for sterilization, as shown in FIG. 1 and FIG. 2. Alternatively, the reaction fermenter 10 can be a fixed tank, a pressure container reinforced in structure, to directly process sterilization by directing a steam.

The spraying duct 44 conducts an inoculation process or adds the liquid nutrient by using a spraying head or a sprinkler. For convenience in arrangement and assembly of the movable layer rack 20, the spraying duct 44 can be easily removed from the fluid pipe 41.

The dry circulation unit 60 is able to connect with a vacuum dryer (not shown in the figures) through the hot dry gas outlet 62 for processing vacuum-drying, if the reaction fermenter 10 is a pressure container.

In FIG. 1 and FIG. 2, the omni-functional solid-state fermentation device 100 is an integrally formed reaction fermenter 10, which has an opening lid 12 at the front side of the reaction fermenter 10. On using the device, the cultivation substrate 1 is filled in the cultivation plate 30 on a platform in advance to be placed on the movable layer rack 20 which is hollowed out at bottom. A plurality of the cultivation plates 30 are stacked on the supporting layers one by one according to requirement. Then, the movable layer rack 20 together with the cultivation plates 30 is pushed into the reaction fermenter 10. The spraying ducts 44 are assembled on the fluid pipe 41. After the opening lid 12 is closed, the reaction fermenter 10 is moved into the tunnel sterilizer (not shown in the figures) for sterilization. After the sterilization, the reaction fermenter 10 is placed still for cooling. An inoculum liquid tank (not shown in the figures) is connected to the fluid inlet 43 on top of the reaction fermenter 10 to direct inoculum liquid into the fluid pipe 41 to be further sprinkled evenly on the cultivation substrate 1 of each layer of the cultivation plate 30 through the spraying ducts 44. The residual part of the inoculum liquid is drained away through the fluid outlet 42 at bottom of the reaction fermenter 10. Then, the omni-functional solid-state fermentation device 100 is moved to a cultivation room, where a sterilized air is directed from the gas inlet 53 at bottom of the reaction fermenter 10 and exhausted from the gas outlet 52 on top of the reaction fermenter 10. During cultivation, a moistened air is directed through the gas pipe 51 to maintain humidity, control temperature, and dissipate heat of the reaction fermenter 10. Preferably, air concentration is adjusted according to aerobic property required for providing the most proper fermentation condition to the microorganisms. The fluid pipe 41 is used for increasing nutrient in the cultivation substrate 1 and achieving a fermentation condition with high efficiency by adding an alkaline fluid nutrient and further adjusting a pH value. Therein, during fermentation and cultivation, the fermentation state can be examined through the observation window 11 at a lateral side of the reaction fermenter 10. After fermentation, the fermented product does not have to be taken out from the reaction fermenter 10. The heated dry air is directed from the hot dry air inlet 61 into the reaction fermenter 10, so that the hot dry air is evenly distributed over each of the cultivation plate 30 for drying and is exhausted from the hot dry air outlet 62 at a rear side. After drying, the opening lid 12 is opened and the spraying duct 44 is detached. The bottom tray 31 of each of the cultivation plate 30 is drawn out from a front side of the cultivation plates 30 one by one from bottom to top. In FIG. 3, the dried cultivation substrate 30, which is the finished fermented product, falls off to the funnel-like collection tray 71 at bottom, and then slides off to the collection bucket 72, where collection is accomplished.

Hence, the omni-functional solid-state fermentation device provided according to the present invention effectively integrates production processes of solid-state fermentation, in which the simple fermentation structure having trays is adopted for sterilization, inoculation, cultivation, drying and collection without the need of transferring fermented products between stations. Contamination rate is largely reduced in the production process; and, there is no need to purchase automatic production equipments of high mechanical technologies. The present invention largely reduces labor requirement with a simple device and an integrated production procedure for mass production with a considerably low production cost. In this manner, a high efficiency may be achieved. Furthermore, it saves time and energy, reduces cost of automatic equipments, uses a simple operation having a low contamination rate, and processes automatic mass production even without automatic production equipments.

To sum up, the present invention is an omni-functional high-efficient solid-state fermentation method for edible and medicinal microorganisms, where a simple fermentation device with trays is provided to integrate sterilization, inoculation, cultivation, drying, and collection for reducing labor requirement, saving time and energy, reducing cost of automatic equipments, achieving low contamination rate, and processing automatic mass production even without automatic production equipments.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. An omni-functional high-efficient solid-state fermentation method for edible and medicinal microorganisms, comprising steps of:
    (a) providing a solid-state fermentation device processing solid-state fermentation and comprising:
    a reaction fermenter having an observation window at a first side and an opening lid at a second side;
    a movable layer rack located in said reaction fermenter; hollowed out at bottom; and having a plurality of supporting layers;
    a corresponding plurality of cultivation plates wherein each cultivation plate is located on a corresponding supporting layer and has a bottom tray;
    a fluid pipeline located in said reaction fermenter and comprising a fluid pipe having a fluid inlet connected with a plurality of spraying ducts wherein every one of said spraying ducts is located above a corresponding one of said supporting layers, separately and a fluid outlet connected to a bottom of the reaction fermenter;
    a gas pipeline located in said reaction fermenter and comprising a gas pipe having a gas inlet connected with a plurality of gas ducts wherein every one of said gas ducts is located between two adjacent ones of said supporting layers, separately and a gas outlet connected to a top of the reaction fermenter;
    a dry circulation unit comprising a hot dry gas inlet located at the second side of the reaction fermenter, a hot dry gas outlet located at a side opposite to the second side of the reaction fermenter, and a plurality of hot gas distribution holes located at the second side of the reaction fermenter and at the side opposite to the second side of the reaction fermenter and with each hot gas distribution hole corresponding to at least one cultivation plate to provide hot dry gas uniformly distributed to each of the cultivation plates; and
    a product collection unit comprising a collection tray located at bottom in said reaction fermenter and inclined inwardly;
    (b) providing a plurality of cultivation substrates, wherein every one of said cultivation substrates is filled in a corresponding one of said cultivation plates, separately;
    (c) directing a fluid into said fluid pipe through said fluid inlet; dividing said fluid into each of said spraying ducts; uniformly spraying said fluid on each of said cultivation plates by each of said spraying ducts to supply inoculums or provide liquid nutrient required on fermenting microorganisms; and leaking out any residual portion of said fluid through said fluid outlet at bottom in said reaction fermenter;
    (d) directing a gas into said gas pipe through said gas inlet; dividing said gas into each of said gas ducts; uniformly spreading said gas on each of said cultivation plates by each of said gas ducts to provide said gas, control temperature, dissipate heat required on fermenting microorganisms; and leaking out any residual portion of said gas through said gas outlet on top in said reaction fermenter; and
    (e) examining a fermenting state and a growth state of microorganisms, processing a drying process after fermenting microorganisms, and collecting dried cultivation substrate by using said product collection unit to obtain a fermented product.

2. The method according to claim 1, wherein said reaction fermenter is formed integrally and has a shape selected from a group consisting of a cylinder shape and a rectangular shape.

3. The method according to claim 1, wherein said reaction fermenter is a movable tank having a wheel to move to a tunnel sterilizer to process sterilization.

4. The method according to claim 1, wherein said reaction fermenter is a fixed tank, a pressure container reinforced in structure, to directly process sterilization by directing a steam.

5. The method according to claim 1, wherein said spraying ducts comprise a spraying head or sprinkler and are detachably connected to said fluid pipe to process an action selected from a group consisting of processing inoculation and adding a liquid nutrient.

6. The method according to claim 1, wherein said reaction fermenter is a pressure container having said hot dry gas inlet connected to a vacuum pipe to process vacuum-drying.

7. The method according to claim 1, wherein said product collection unit further comprises a collection bucket; and wherein said bottom tray of said cultivation plate located in said layer rack is drawn out from a side of said cultivation plate to have said dried cultivation substrate fall off onto said collection tray to be collected into said collection bucket.

\* \* \* \* \*